(12) United States Patent
Sweitzer et al.

(10) Patent No.: US 12,109,129 B2
(45) Date of Patent: Oct. 8, 2024

(54) SURGICAL EXTRACTOR

(71) Applicant: Shukla Medical, St. Petersburg, FL (US)

(72) Inventors: Zachary Robert Sweitzer, Keyport, NJ (US); Adam Gosik-Wolfe, Tampa, FL (US)

(73) Assignee: Shukla Medical, St. Petersburg, FL (US)

( * ) Notice: Subject to any disclaimer, the term of this patent is extended or adjusted under 35 U.S.C. 154(b) by 190 days.

(21) Appl. No.: 17/148,933

(22) Filed: Jan. 14, 2021

(65) Prior Publication Data

US 2021/0212840 A1    Jul. 15, 2021

Related U.S. Application Data

(60) Provisional application No. 62/960,979, filed on Jan. 14, 2020.

(51) Int. Cl.
*A61F 2/46* (2006.01)
*A61B 17/92* (2006.01)

(52) U.S. Cl.
CPC ............ *A61F 2/4612* (2013.01); *A61B 17/92* (2013.01); *A61F 2/4603* (2013.01); *A61F 2002/4619* (2013.01); *A61F 2002/4622* (2013.01); *A61F 2002/4627* (2013.01)

(58) Field of Classification Search
CPC ........ A61F 2002/4619; A61F 2002/462; A61F 2002/4622; A61F 2002/4625; A61F 2002/4627; A61F 2002/4628; A61F 2/4607; A61F 2/4612; A61F 2/4603; A61B 17/92
See application file for complete search history.

(56) References Cited

U.S. PATENT DOCUMENTS

| | | | | |
|---|---|---|---|---|
| 1,534,992 | A | * | 4/1925 | Reeves ..................... B66F 3/22 254/126 |
| 5,282,805 | A | * | 2/1994 | Richelsoph ........... A61F 2/4607 606/100 |
| 6,017,342 | A | * | 1/2000 | Rinner ............... A61B 17/8866 606/57 |
| 2004/0059271 | A1 | * | 3/2004 | Berry ........................ A61F 2/44 602/32 |
| 2005/0033290 | A1 | * | 2/2005 | Nevelos ............... A61B 17/175 606/53 |
| 2005/0209597 | A1 | * | 9/2005 | Long .................... A61F 2/4609 606/86 R |

(Continued)

*Primary Examiner* — Amy R Sipp
(74) *Attorney, Agent, or Firm* — Kim IP Law Group LLC

(57) ABSTRACT

A surgical extractor including first and second arms connected to first and second implant-engageable jaws. The first and second arms are connected by first and third links to a stationary screw jack nut and by second and fourth links to a moveable screw jack nut. A driven shaft is rotatably received in the stationary screw jack nut and threadedly received in the moveable screw jack nut, and a drive shaft rotatably drives the driven shaft. Rotation of the drive shaft in a first direction separates the first and second arms and jaws in order to receive an implant. Rotation of the drive shaft in a second direction closes the first and second arms and jaws in order to clamp an implant. A handle assembly engages the drive shaft in order to drive the drive shaft and disengages from the drive shaft to exert a removal force on an implant.

18 Claims, 22 Drawing Sheets

(56) References Cited

U.S. PATENT DOCUMENTS

| | | | |
|---|---|---|---|
| 2006/0074432 A1* | 4/2006 | Stad | A61F 2/4611 606/90 |
| 2007/0163084 A1* | 7/2007 | Liou | B25B 23/0035 16/436 |
| 2012/0253469 A1* | 10/2012 | Collins | A61F 2/4603 623/23.15 |
| 2016/0228262 A1* | 8/2016 | Bailey | A61F 2/34 |
| 2018/0125674 A1* | 5/2018 | Liu | A61F 2/4611 |
| 2018/0125677 A1* | 5/2018 | Burrows-Ownbey | A61F 2/447 |

* cited by examiner

SURGICAL EXTRACTOR

CROSS-REFERENCE TO RELATED APPLICATION

This application claims the benefit under 35 U.S.C. § 119(e) to U.S. Provisional Application No. 62/960,979, filed Jan. 14, 2020, and entitled "Medical Device Instrument," the entire disclosure of which is hereby incorporated by reference for all purposes.

BACKGROUND OF THE DISCLOSURE

The exemplary embodiments of present invention relate generally to a surgical extractor and, more specifically, to an instrument for extracting an implant including, without limitation, a glenosphere implant, from bone.

BRIEF SUMMARY OF THE DISCLOSURE

In accordance with an exemplary embodiment there is provided a surgical extractor that includes a first arm having a proximal end and a distal end, a second arm having a proximal end and a distal end, and an adjustment assembly operatively connected to the first and second arms. The adjustment assembly includes first and second links pivotably connected to a first side of the first arm, third and fourth links pivotably connected to a first side of the second arm, and an adjustment mechanism. The adjustment mechanism includes a driven shaft rotatable relative to the first and second arms and operable to move the first arm and the second arm toward and away from the driven shaft by respective pivoting of the first and second links and of the third and fourth links. The adjustment mechanism further includes a drive shaft for driving rotation of the driven shaft.

According to an aspect, the surgical extractor further includes a handle assembly operably attachable to the adjustment mechanism for rotating the drive shaft, a first jaw attachable to the distal end of the first arm, and a second jaw attachable to the distal end of the second arm. According to a further aspect, the handle assembly includes a push-to-connect assembly structured to releasably couple to a proximal end of the drive shaft. According to a further aspect, the drive shaft includes an annular groove adjacent to the proximal end thereof. According to a further aspect, the push-to-connect assembly includes an actuator operable to move transversely to a longitudinal axis of the drive shaft to engage and disengage the annular groove. According to a further aspect, the push-to-connect assembly further includes a biasing member biasing the actuator into engagement with the annular groove. According to a further aspect, the handle assembly includes a T-handle.

According to an aspect, the adjustment assembly further includes fifth and sixth links pivotably connected to a second side of the first arm, and seventh and eighth links pivotably connected to a second side of the second arm. According to a further aspect, the surgical extractor includes a bracket surrounding the first, second, third, fourth, fifth, sixth, seventh and eighth links.

According to an aspect, the driven shaft includes a proximal end and a threaded remainder portion, wherein the proximal end is spaced from the proximal ends of the first and second arms. According to a further aspect, the surgical extractor includes a stationary screw jack nut that rotatably receives the driven shaft, and a moveable screw jack nut that threadedly receives the threaded remainder portion. According to a further aspect, second ends of the first and third links are pivotably connected to the stationary screw jack nut, and second ends of the second and fourth links are pivotably connected to the moveable screw jack nut. According to a further aspect, a proximal end of the driven shaft includes a socket. According to a further aspect, a distal end of the drive shaft includes a cooperating head to engage with the socket of the driven shaft.

According to an aspect, the surgical extractor includes a strike plate including a substantially planar member having a first striking surface and a second striking surface opposite the first striking surface. According to a further aspect, the strike plate additionally includes a multisided through opening configured to receive a multisided shaft portion of the surgical extractor.

According to an aspect, the surgical extractor includes a jaw having a proximal end configured for attachment to the distal end of the first arm and a distal end for engaging an implant. According to a further aspect, the surgical extractor includes a biased latch adjacent the distal end of the first arm for releasably engaging the proximal end of the jaw. According to a further aspect, the surgical extractor includes at least one male member carried by the proximal end of the jaw and at least one female opening at the distal end of the first arm for receiving the at least one male member. According to a further aspect, the biased latch releasably engages the at least one male member. According to a further aspect, the at least one male member includes a notch for receiving the biased latch. According to a further aspect, the biased latch includes a button for moving the biased latch from engagement with the proximal end of the jaw.

Other features and advantages of the subject disclosure will be apparent from the following more detailed description of the exemplary embodiments.

BRIEF DESCRIPTION OF THE SEVERAL VIEWS OF THE DRAWINGS

The foregoing summary, as well as the following detailed description of the exemplary embodiments of the subject disclosure, will be better understood when read in conjunction with the appended drawings. For the purpose of illustrating the present disclosure, there are shown in the drawings exemplary embodiments. It should be understood, however, that the subject application is not limited to the precise arrangements and instrumentalities shown.

DETAILED DESCRIPTION OF THE DISCLOSURE

Figure 1:
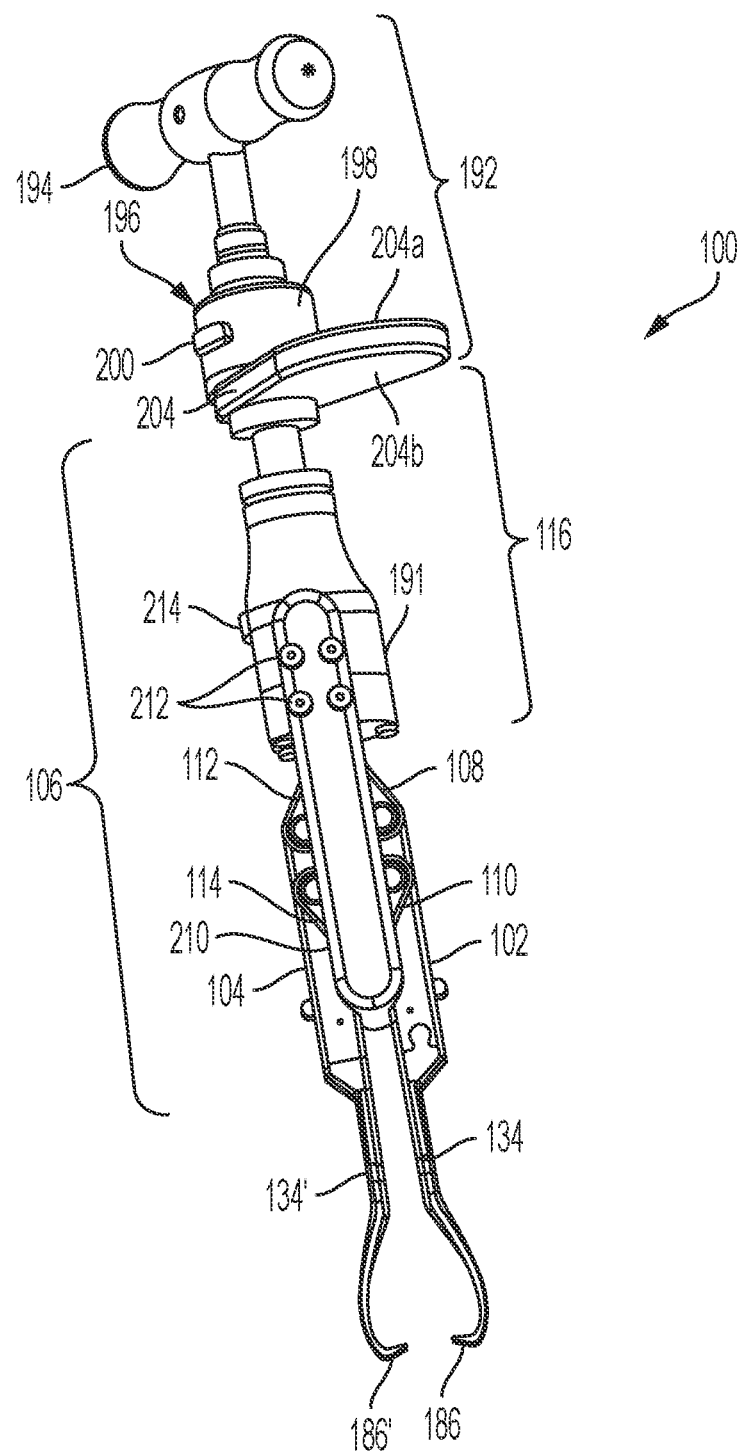
FIG. 1 is a front perspective view of a surgical extractor in accordance with an exemplary embodiment of the subject disclosure.

Reference will now be made in detail to the various exemplary embodiments of the subject disclosure illustrated in the accompanying drawings. Wherever possible, the same or like reference numbers will be used throughout the drawings to refer to the same or like features. It should be noted that the drawings are in simplified form and are not drawn to precise scale. Certain terminology is used in the following description for convenience only and is not limiting. Directional terms such as top, bottom, left, right, above, below and diagonal, are used with respect to the accompanying drawings. The term "distal" shall mean away from the center of a body. The term "proximal" shall mean closer towards the center of a body and/or away from the "distal" end. The words "inwardly" and "outwardly" refer to directions toward and away from, respectively, the geometric center of the identified element and designated parts thereof. Such directional terms used in conjunction with the following description of the drawings should not be construed to limit the scope of the subject application in any manner not explicitly set forth. Additionally, the term "a," as used in the specification, means "at least one." The terminology includes the words above specifically mentioned, derivatives thereof, and words of similar import.

"About" as used herein when referring to a measurable value such as an amount, a temporal duration, and the like, is meant to encompass variations of ±20%, ±10%, ±5%, ±1%, or ±0.1% from the specified value, as such variations are appropriate.

"Substantially" as used herein shall mean considerable in extent, largely but not wholly that which is specified, or an appropriate variation therefrom as is acceptable within the field of art. "Exemplary" as used herein shall mean serving as an example.

Throughout the subject application, various aspects thereof can be presented in a range format. It should be understood that the description in range format is merely for convenience and brevity and should not be construed as an inflexible limitation on the scope of the subject disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Furthermore, the described features, advantages and characteristics of the exemplary embodiments of the subject disclosure may be combined in any suitable manner in one or more embodiments. One skilled in the relevant art will recognize, in light of the description herein, that the subject disclosure can be practiced without one or more of the specific features or advantages of a particular exemplary embodiment. In other instances, additional features and advantages may be recognized in certain embodiments that may not be present in all exemplary embodiments of the present disclosure.

Figure 2:
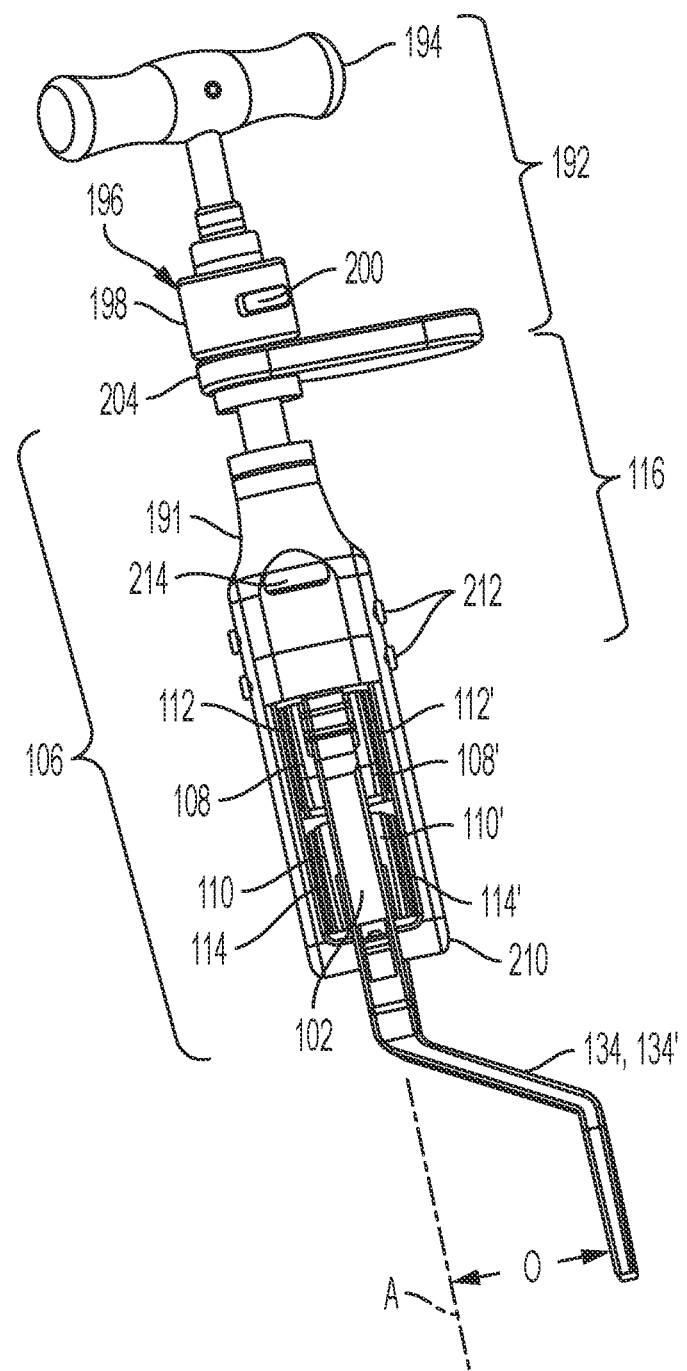
FIG. 2 is a side perspective view of the surgical extractor of FIG. 1.
Figure 3:
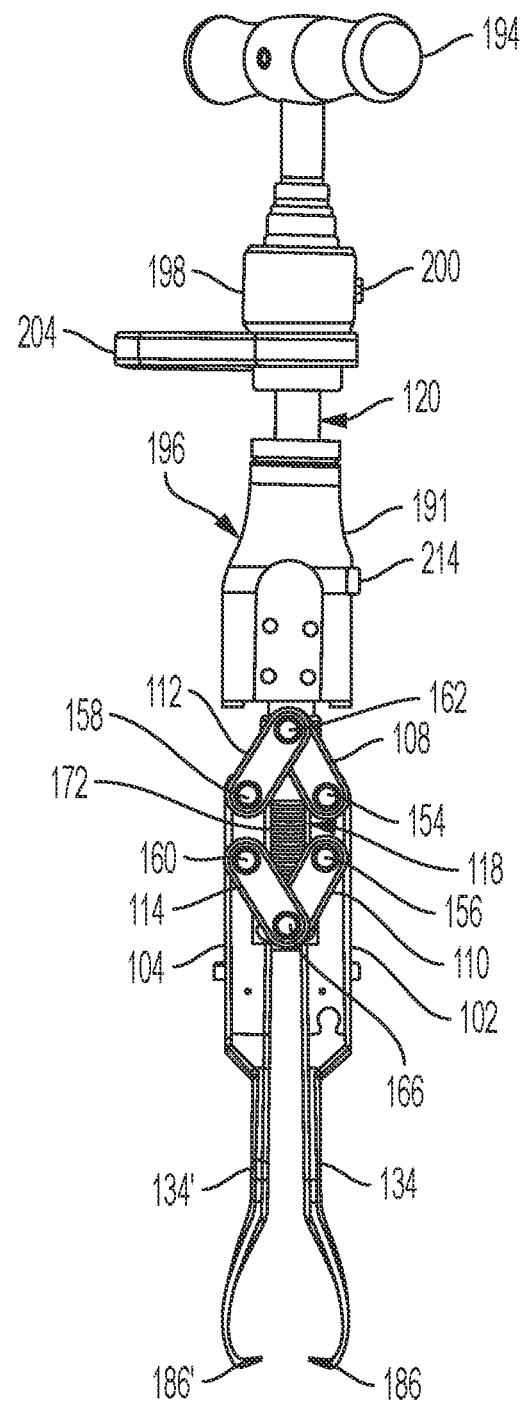
FIG. 3 is another front perspective view of the surgical extractor of FIG. 1 with certain elements omitted for clarity of illustration.
Figure 4:
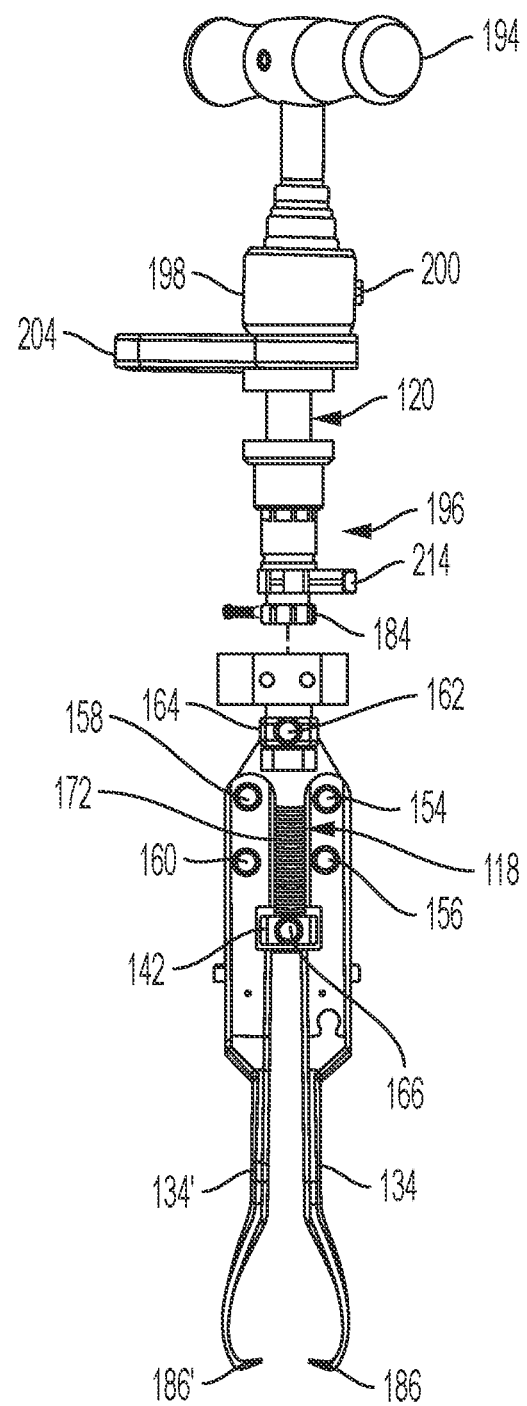
FIG. 4 is another front elevation view of the surgical extractor of FIG. 1 with certain elements omitted for clarity of illustration.

Referring now to the drawings, FIGS. 1 and 2 illustrate a surgical extractor 100 in accordance with an exemplary embodiment of the present disclosure. The surgical extractor 100 comprises a first arm 102, a second arm 104, and an adjustment assembly 106 operatively connected to the first and second arms. The adjustment assembly includes first and second links 108, 110 pivotably connected to a first side of the first arm, and third and fourth links 112, 114 pivotably connected to a first side the second arm. Further, as shown in FIG. 2, the adjustment assembly additionally comprises fifth and sixth links 108', 110' pivotably connected to a second side of the first arm, and seventh and eighth links 112', 114' pivotably connected to a second side the second arm. The adjustment assembly 106 is operatively connected to the first and second arms and comprises an adjustment mechanism 116 operatively connected to the first, second, third, fourth, fifth, sixth, seventh and eighth links. The adjustment mechanism includes a driven shaft 118 (FIG. 4) and a drive shaft 120 (FIG. 4). As described in greater detail below, the driven shaft is rotatable relative to the first and second arms and operable to move the first arm and the second arm toward and away from the driven shaft by respective pivoting of the first and second links and of the third and fourth links. The drive shaft 120 drivingly rotates the driven shaft 118.

Figure 9:
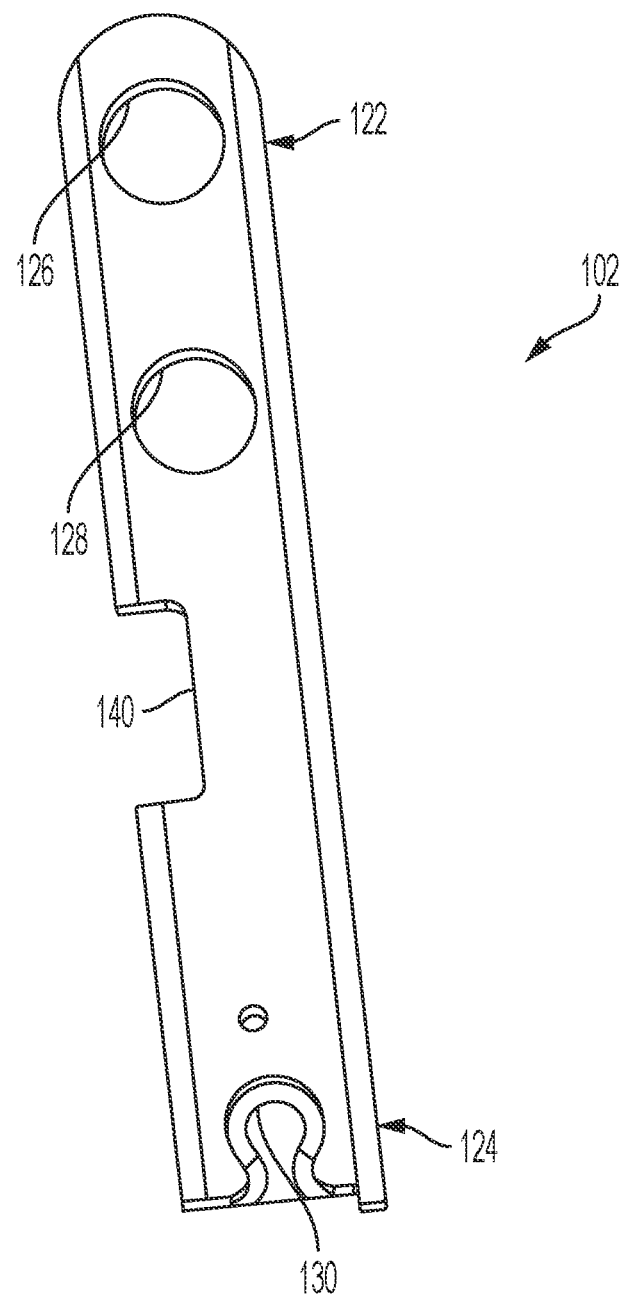
FIG. 9 is a front perspective view of a first arm of the surgical extractor of FIG. 1.
Figure 10:
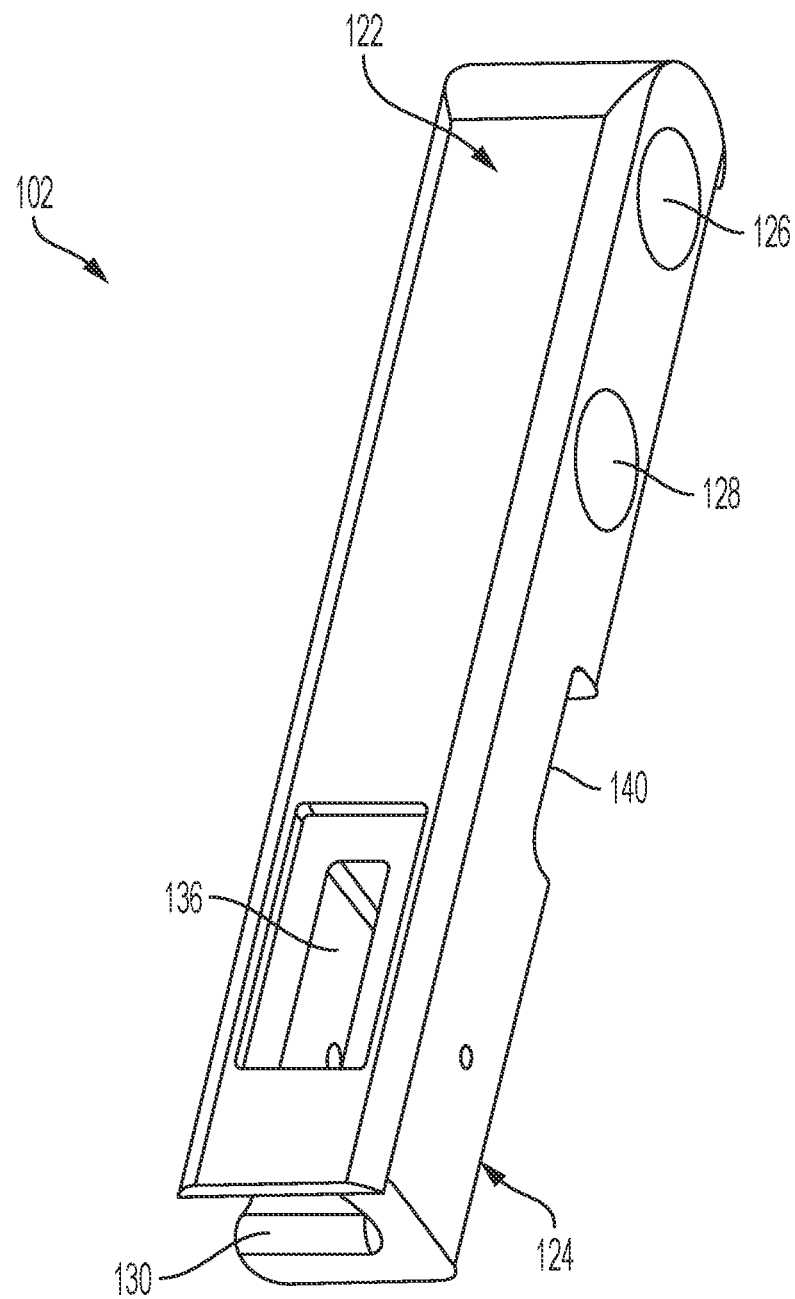
FIG. 10 is a side perspective view of the first arm of the surgical extractor of FIG. 1.

The first arm 102 is configured as best shown in FIGS. 9 and 10 and has a proximal end 122 and a distal end 124. The proximal end 122 includes first and second holes 126, 128 for receiving pivots, e.g., pins, described below, for pivotably connecting the first and second links 108, 110 to the first arm. The distal end 124 includes at least one female opening 130 for receiving at least one male member 132 of a first implant engageable jaw 134 (FIG. 19), as described below. The distal end further includes a slot 136 for receiving a biased latch 138 (FIG. 6) for releasably engaging the proximal end of the jaw, as described below. The first arm 102 also includes a generally centrally located notch 140 about its medial side for accommodating a portion of an internally threaded movable screw jack nut 142 (FIGS. 4, 5, 7, 13 and 14), as further described below.

Figure 11:
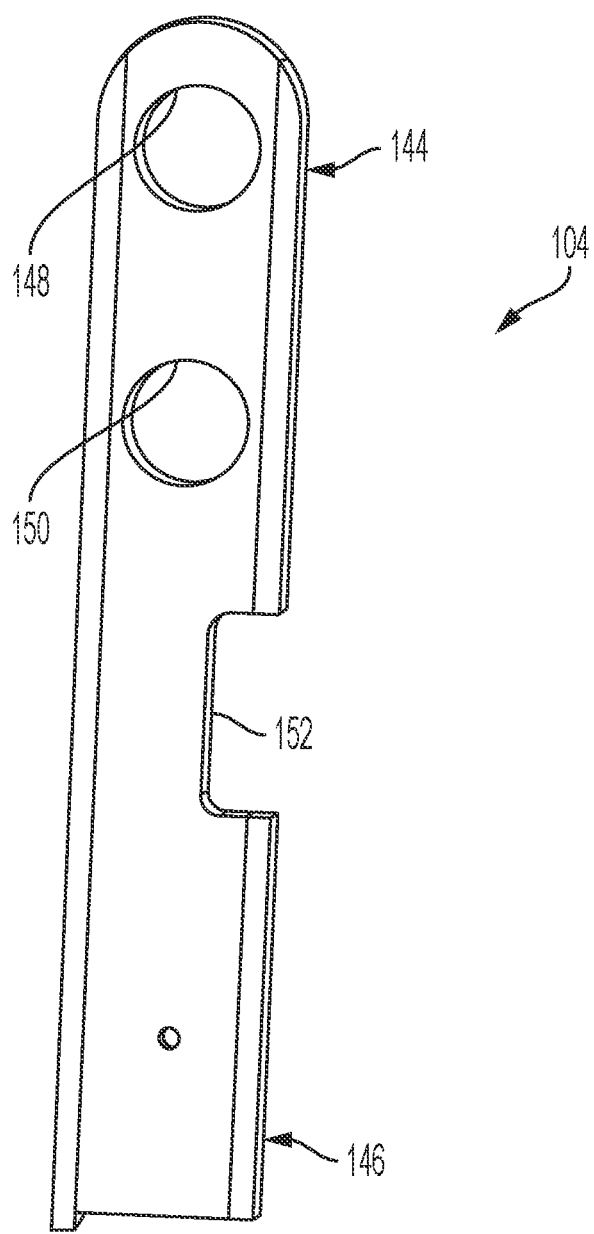
FIG. 11 is a front perspective view of a second arm of the surgical extractor of FIG. 1.
Figure 12:
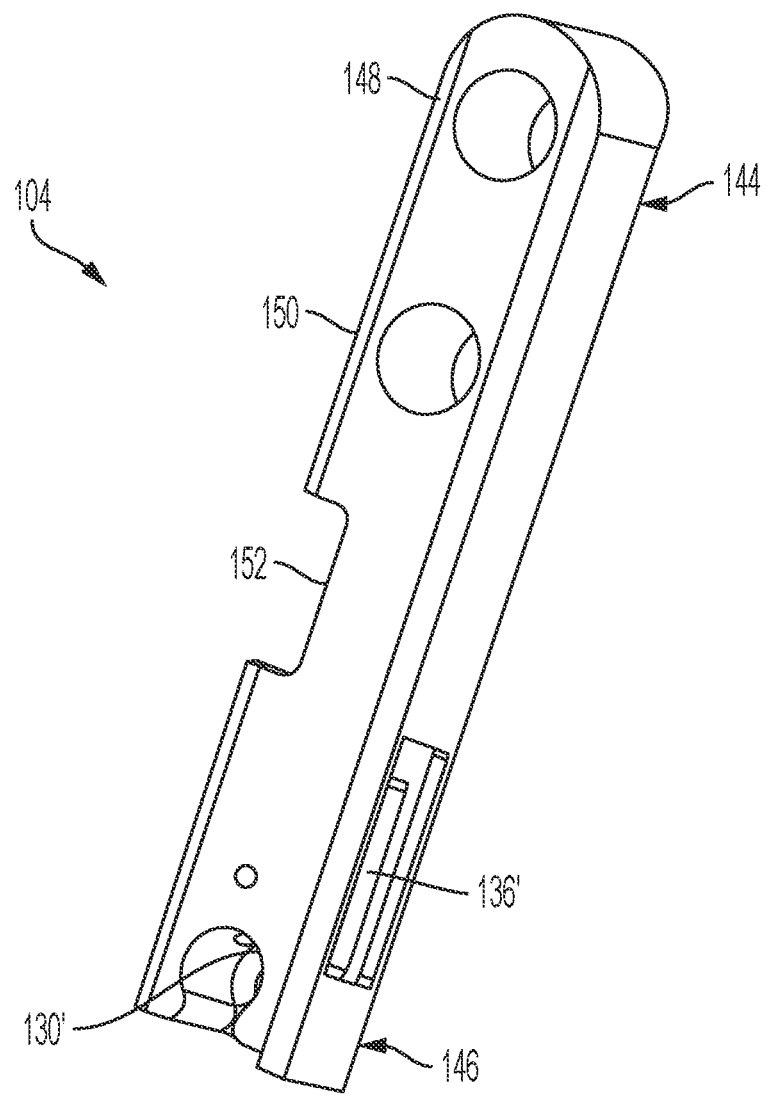
FIG. 12 is a side perspective view of the second arm of the surgical extractor of FIG. 1.
Figure 20:
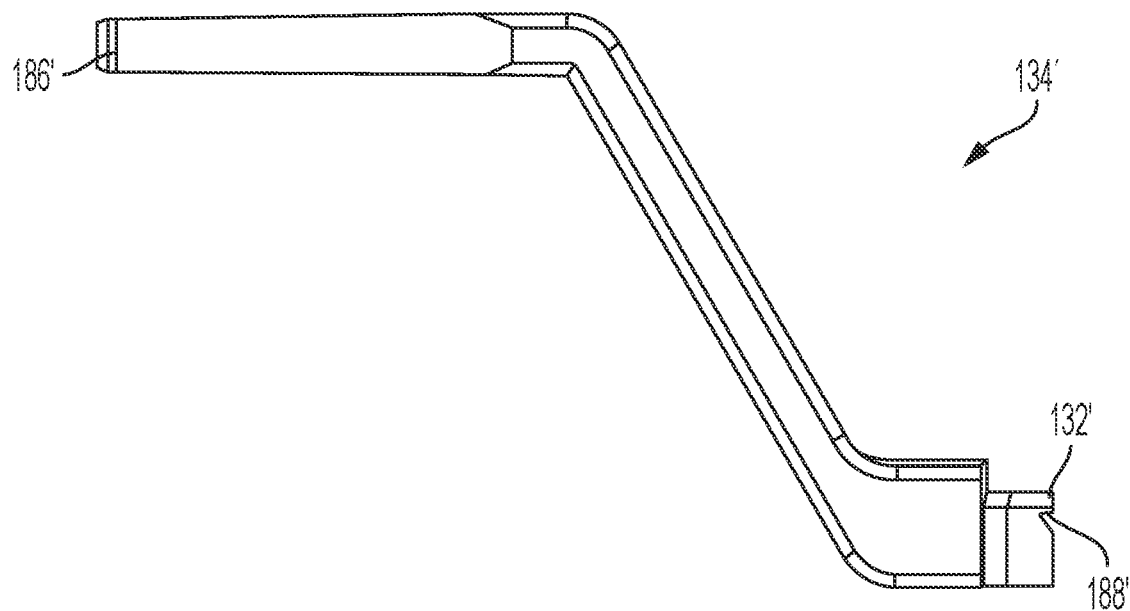
FIG. 20 is a perspective view of a second implant engageable jaw of the surgical extractor of FIG. 1.

The second arm 104 is configured as best shown in FIGS. 11 and 12 and has a proximal end 144 and a distal end 146. The proximal end 144 includes first and second holes 148, 150 for receiving pivots, e.g., pins, described below, for pivotably connecting the third and fourth links 112, 114 to the second arm. The distal end 146 includes at least one female opening 130' for receiving at least one male member 132' of a second implant engageable jaw 134' (FIG. 20), as described below. The distal end further includes a slot 136' for receiving a biased latch 138' (FIGS. 6 and 6A) for releasably engaging the proximal end of the jaw, as described below. The second arm 104 also includes a generally centrally located notch 152 about its medial side for accommodating a portion of the movable screw jack nut 142, as described below.

The first, second, third and fourth links are configured as best shown in FIGS. 3, 6, 8 and 15. Each link is generally oval in shape and has first and second ends with openings for receiving pivots, e.g., pins or stub shafts, for pivotably connecting the links to the pins or stub shafts, as described in greater detail below.

Referring to FIGS. 3, 5, 6, 8 and 15, the first ends of the first and second links 108, 110 are pivotably connected to the first arm 102 by pins 154, 156 which pass through the holes 126, 128 in the first arm 102. Similarly, the first ends of the third and fourth links 112, 114 are pivotably connected to the second arm 104 by pins 158, 160 which pass through the holes 148, 150 in the second arm 104. The second ends of the first and third links 108, 112 are pivotably connected to a stationary screw jack nut 164 (FIG. 7) that rotatably receives a driven shaft 118. In particular, the second ends of the first and third links are pivotably connected to a stub shaft 162 (FIG. 13) projecting from a side of the stationary screw jack nut. Similarly, second ends of the second and fourth links 110, 114 are pivotably connected to the movable screw jack nut 142, particularly to a stub shaft 166 projecting from a side of the movable screw jack nut.

Figure 13:
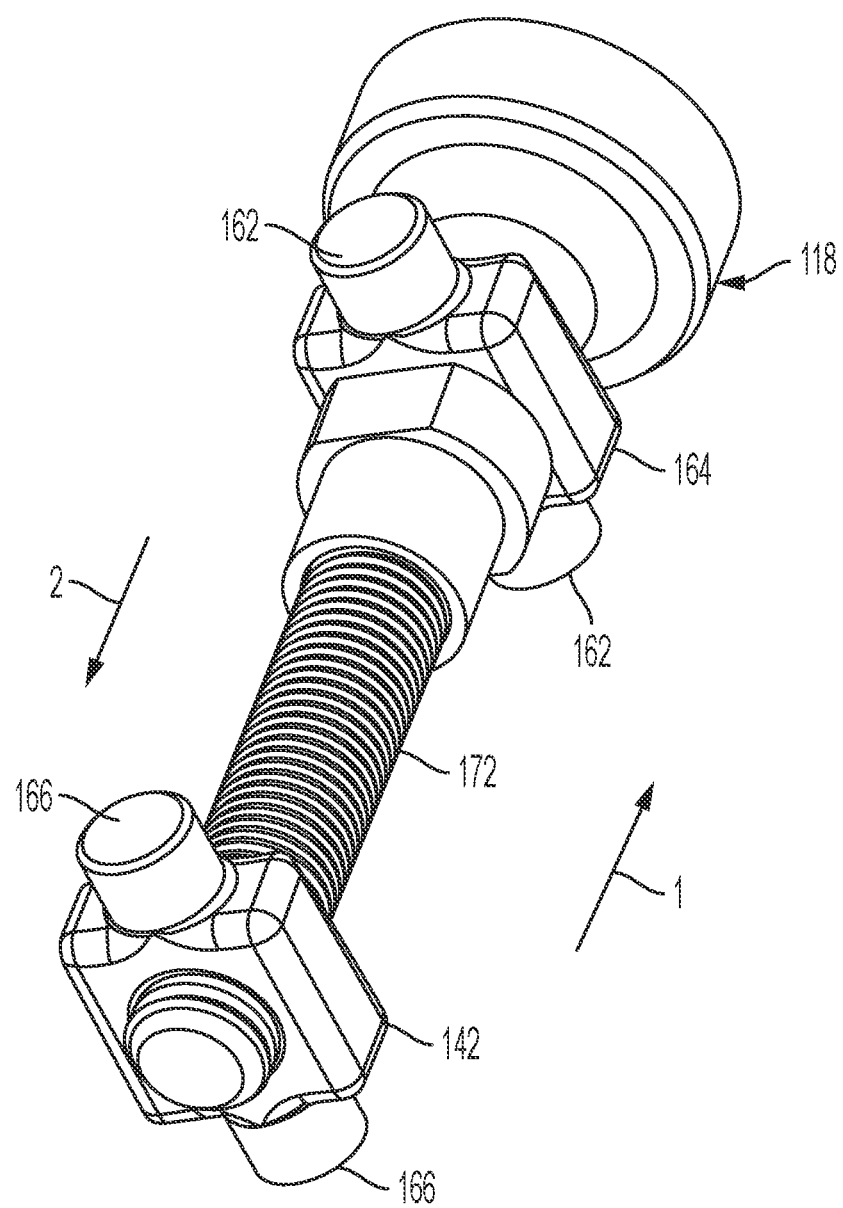
FIG. 13 is a perspective view of a portion of an adjustment assembly of the surgical extractor of FIG. 1.
Figure 14:
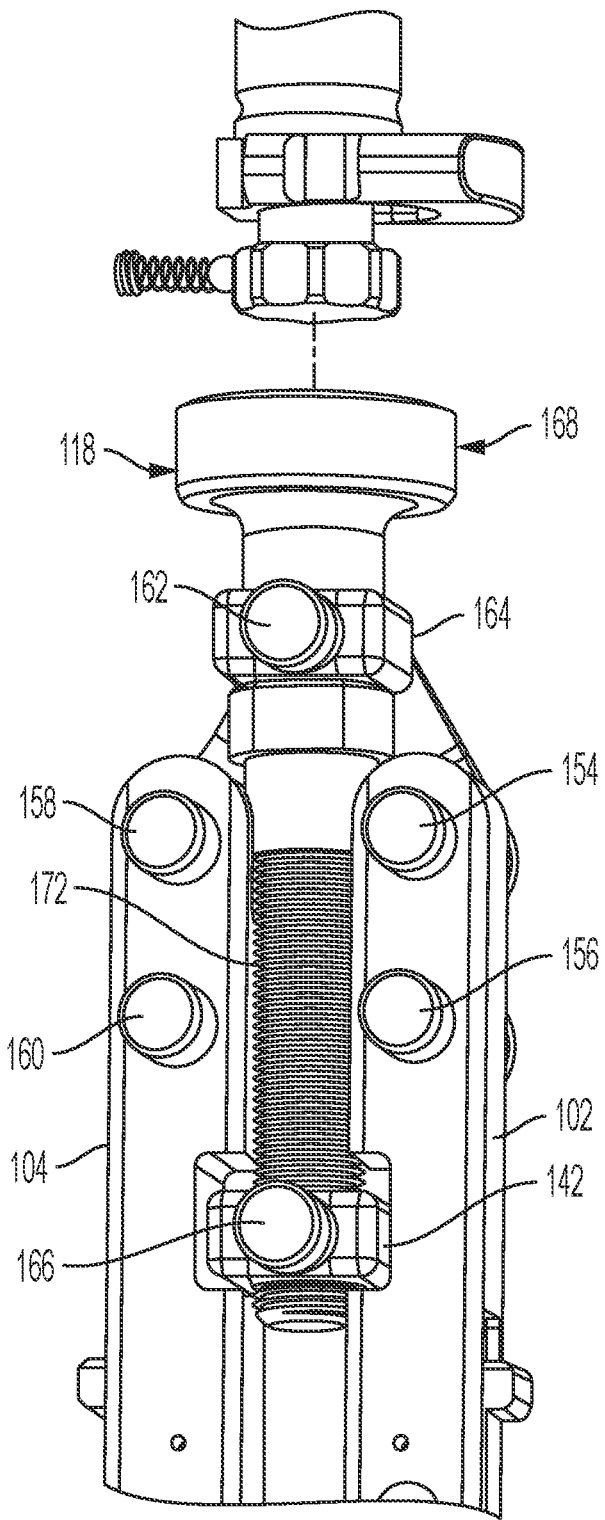
FIG. 14 is a partial front perspective view of a portion of an adjustment assembly of the surgical extractor of FIG. 1.
Figure 15:
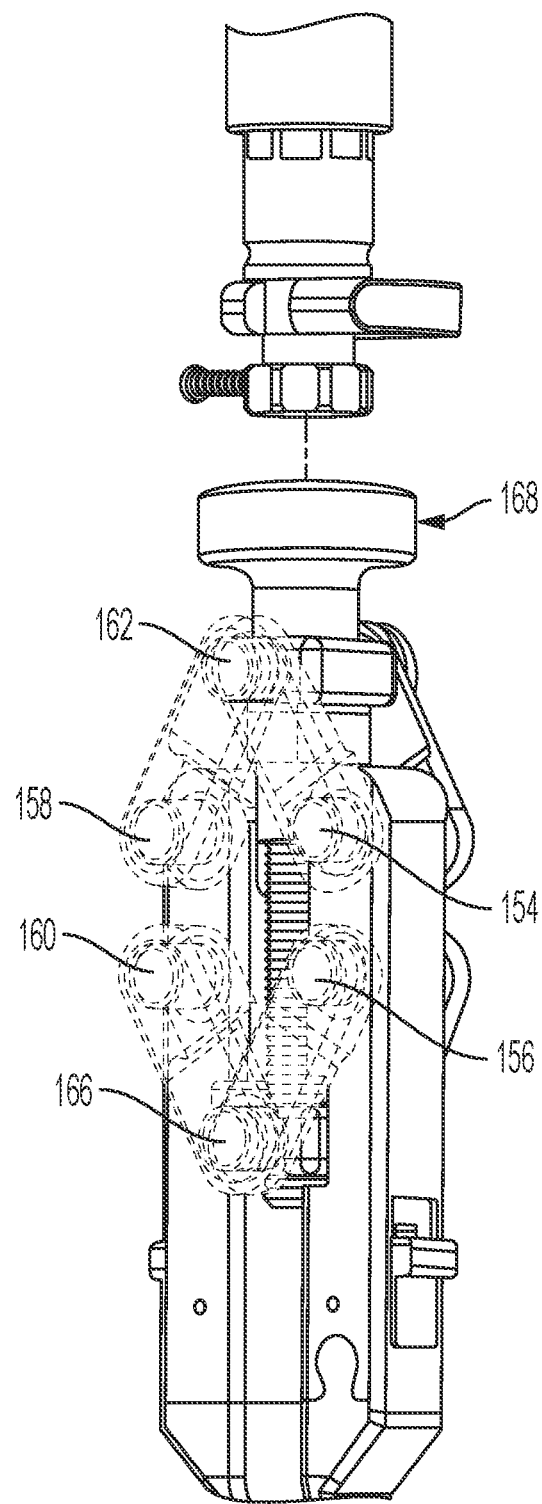
FIG. 15 is a partial side perspective view of a portion of an adjustment assembly of the surgical extractor of FIG. 1 with certain elements in phantom for clarity of illustration.
Figure 16:
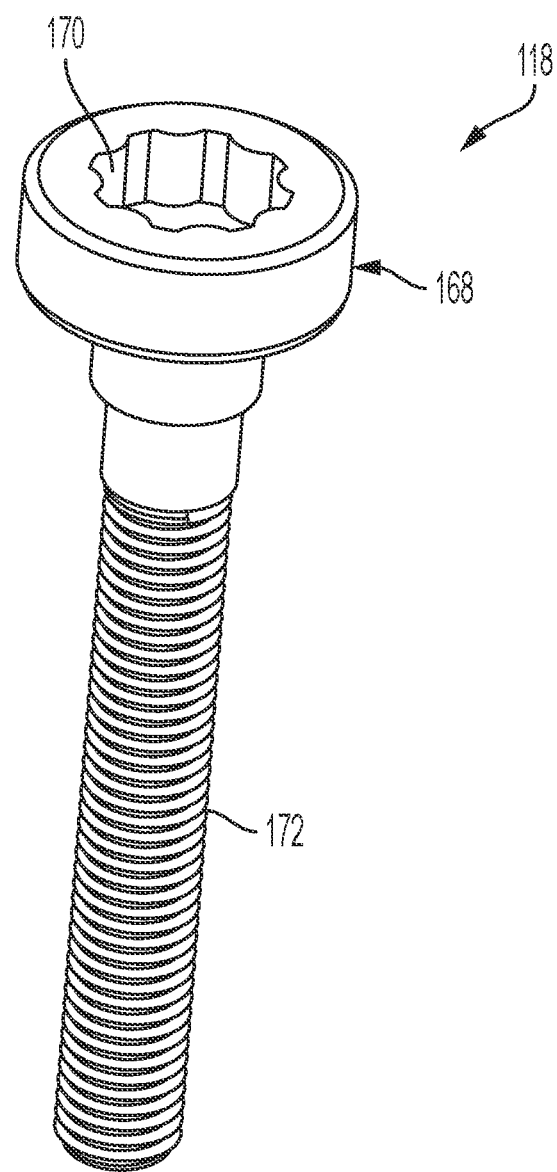
FIG. 16 is a perspective view of a driven shaft of the adjustment assembly of the surgical extractor of FIG. 1.

Referring to FIGS. 13, 14 and 16, the driven shaft 118 includes a proximal end 168 defining a socket 170. The driven shaft further includes a threaded remainder portion, as indicated by reference numeral 172. As shown in FIG. 15, the proximal end 168 of the driven shaft is spaced from the proximal ends of the first and second arms 102, 104. The driven shaft is rotatable relative to the first and second arms, and the drive shaft 120 (FIG. 4) is configured for driving rotation of the driven shaft. The driven shaft remains stationary relative to the movement of the first and second arms and their respective pivot links.

Figure 5:
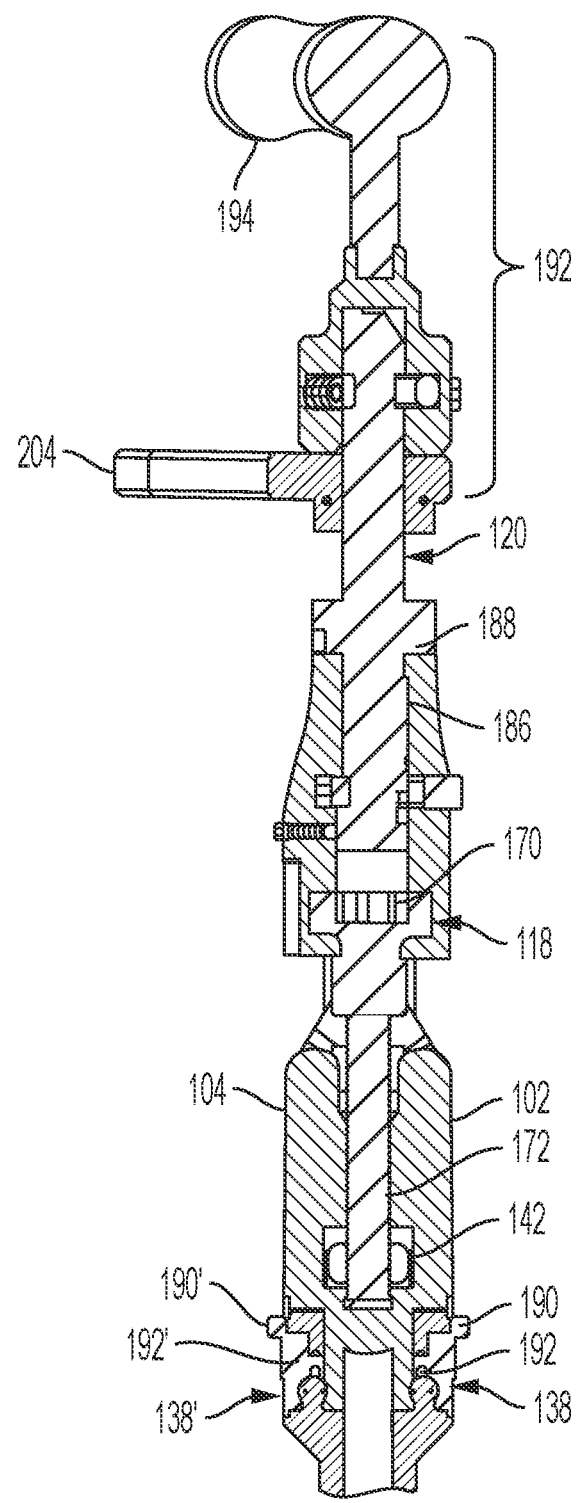
FIG. 5 is a longitudinal front cross-sectional view of the surgical extractor of FIG. 1.
Figure 7:
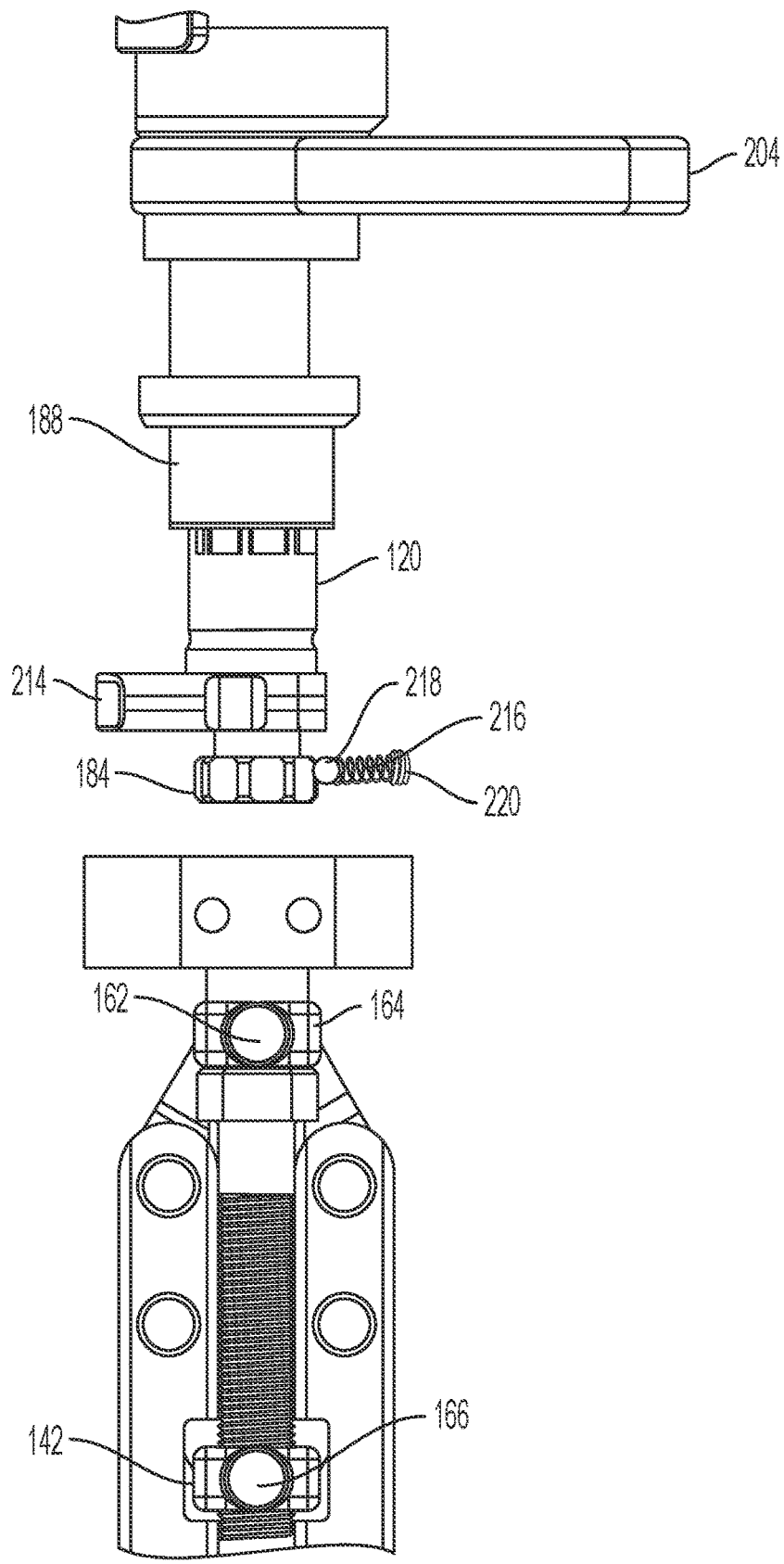
FIG. 7 is another enlarged partial front view of the surgical extractor of FIG. 1 with certain elements omitted for clarity of illustration.
Figure 8:
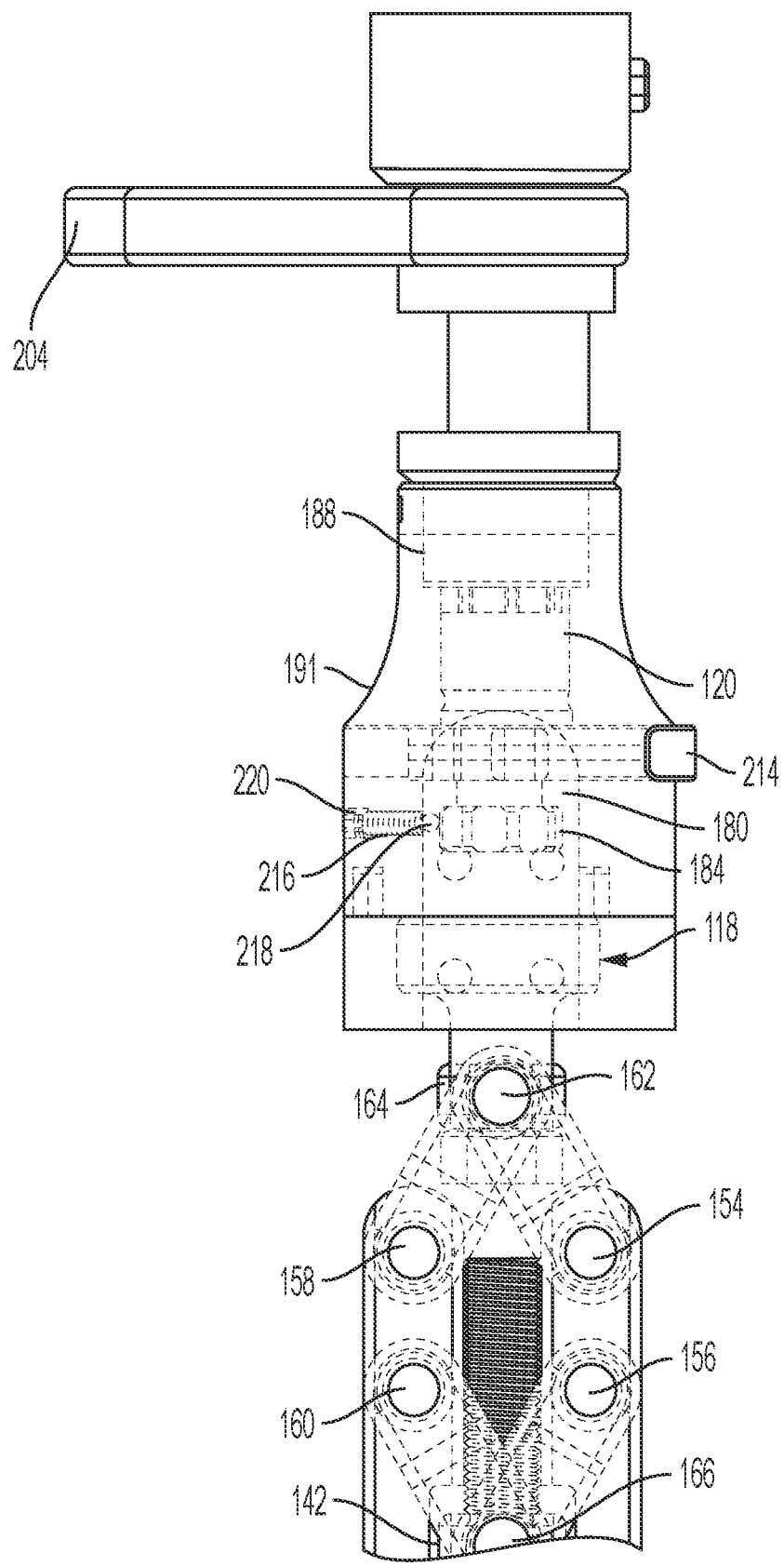
FIG. 8 is another enlarged partial front view of the surgical extractor of FIG. 1 with certain elements omitted for clarity of illustration.
Figure 17:
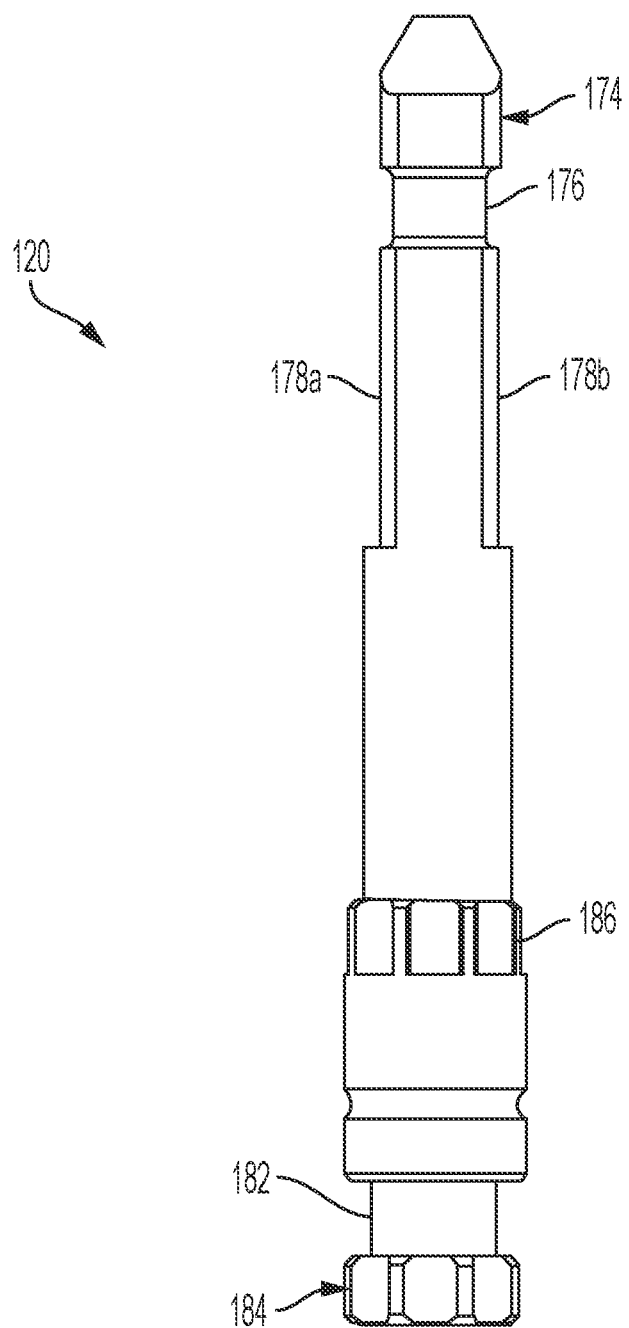
FIG. 17 is a side view of a drive shaft of the adjustment assembly of the surgical extractor of FIG. 1.

The drive shaft 120 is shown in FIGS. 5, 7 and 8, and is configured as best shown in FIG. 17. The drive shaft includes a proximal end 174 and an annular groove 176 adjacent the proximal end. The drive shaft further includes a pair of oppositely facing flats 178a, 178b. The distal end 180 of the drive shaft includes another annular groove 182 and a cooperating head 184 configured to engage with the socket 170 of the driven shaft 118. According to an aspect, the socket 170 can be internally splined and the cooperating head 184 can be externally splined. About a mid-portion, the drive shaft includes a second spline 186 for engaging a similarly splined bushing 188 (FIGS. 4, 5, 7 and 8) that is rotatable in a second housing 191 (FIGS. 1-3), described below.

Referring back to FIG. 1, the surgical extractor 100 further comprises a handle assembly 192 operably attachable to the adjustment mechanism for rotating the drive shaft 120. The handle assembly can include a T-handle 194.

Referring to FIGS. 1-4 and 18, the handle assembly 192 further includes a push-to-connect assembly 196 structured to releasably couple to a proximal end of the drive shaft. The push-to-connect assembly 196 includes a first housing 198. According to an aspect, the T-handle 194 can be releasably coupled to the drive shaft 120 by an actuator 200 operable to move in the housing 198 transversely to a longitudinal axis of the drive shaft to engage and disengage the annular groove 176 on the drive shaft (FIG. 17). The push-to-connect assembly 196 further comprises a biasing member, e.g., a spring 202, biasing the actuator 200 into engagement with the annular groove 176 of the drive shaft 120 to retain the T-handle 194 on the drive shaft. Attachment and removal of the first housing and the T-handle are described below.

Figure 22:
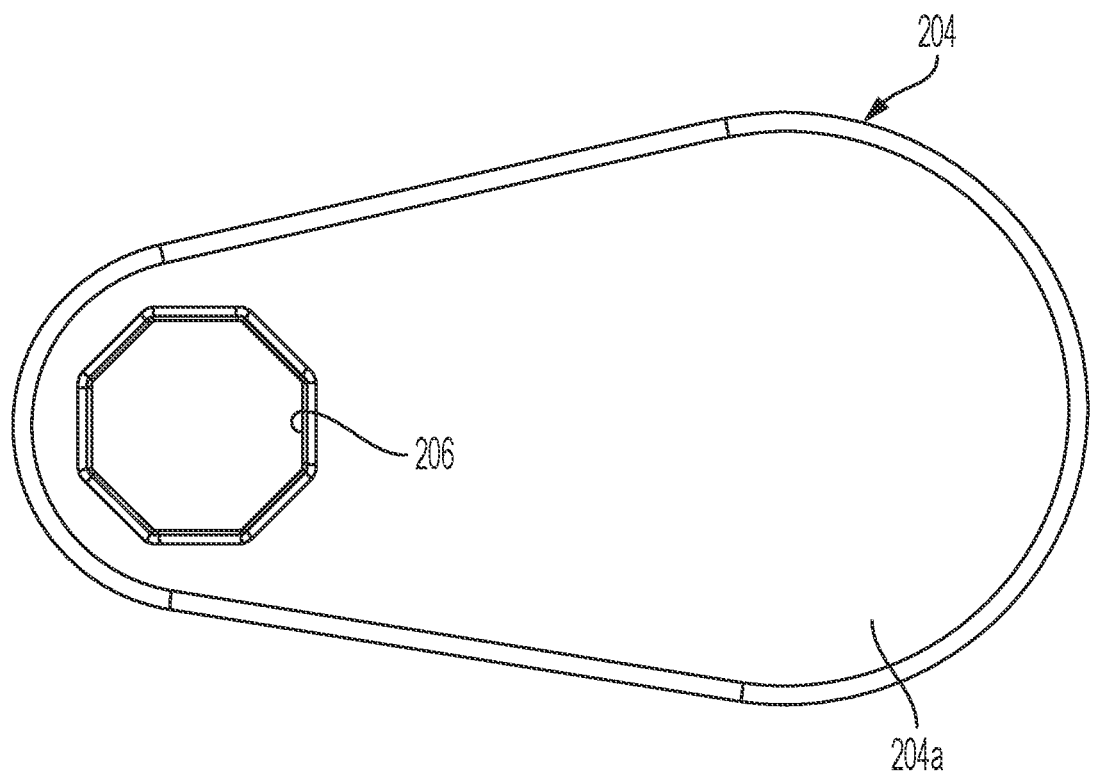
FIG. 22 is a top plan view of a strike plate of the surgical extractor of FIG. 1.

As shown in FIGS. 1-8, the handle assembly 192 further comprises a strike plate 204 projecting laterally from the surgical extractor. As shown in FIG. 1, the strike plate is a substantially planar member having a first striking surface 204a and a second striking surface 204b opposite the first striking surface. As shown in FIG. 22, the strike plate further includes a through opening 206 configured to receive a shaft portion 208 of the surgical extractor (FIG. 18), in particular the drive shaft 120. The through opening can be a multisided opening, i.e., a polygonal shaped opening, e.g., hexagonal or, as illustrated, octagonal in shape. The shaft portion is configured to seat within the multisided through opening, i.e., the shaft portion is complementary shaped with the multisided through opening. The cooperating relationship between the multisided through opening 206 of the strike plate and the multisided shaft portion 208 of the surgical extractor enables the strike plate to be positioned at several angular positions about the longitudinal axis A (FIG. 2) of the surgical extractor as the user may desire. The strike plate 204 is provided to be struck, typically on its second striking surface 204b, by a striking tool such as a mallet, hammer or the like, in order to extract an implant from bone, as described below.

Figure 19:
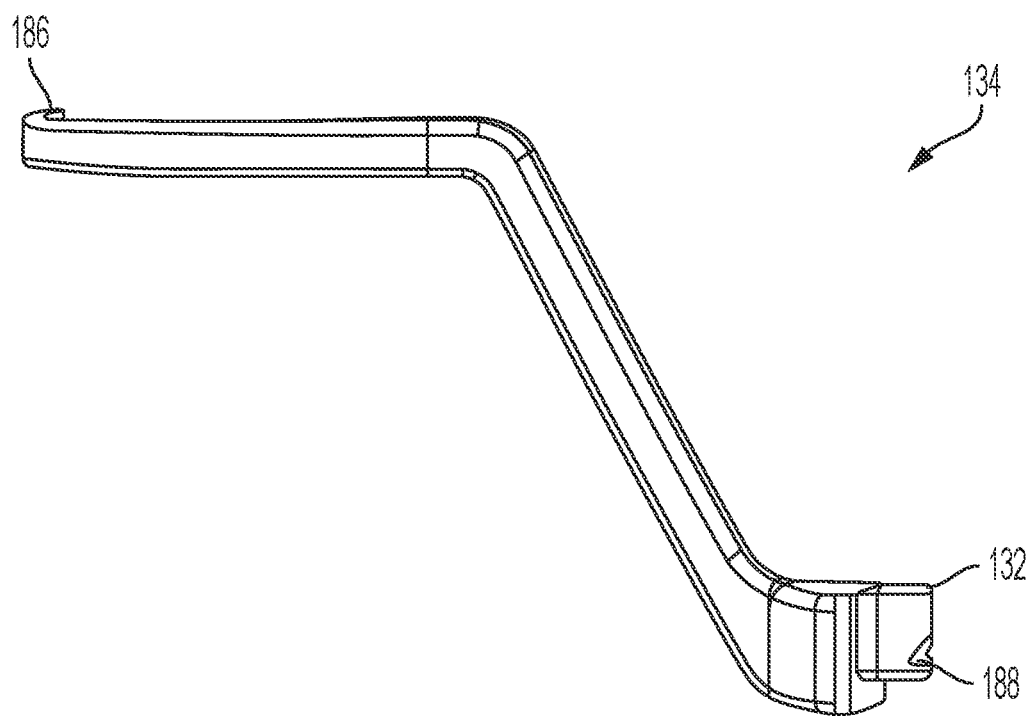
FIG. 19 is a perspective view of a first implant engageable jaw of the surgical extractor of FIG. 1.

Referring to FIG. 19, there is shown a first jaw 134 having a proximal end attachable to the distal end 124 of the first arm 102 and a distal end configured for engaging an implant. A similarly constructed second jaw 134' (FIG. 20) is releasably attachable to the distal end 146 of the second arm 104 in opposition to the first jaw. More particularly, the first and second jaws are attached to opposed sides of the first and second arms such that engagement structures thereof, described below, are positioned to engage an implant to be extracted. Each proximal end of the jaws 134, 134' includes at least one male member 132, 132' carried by the proximal end of the jaw and configured to be received within at least one female opening 130, 130' provided at the distal ends of the first and second arms. Each of the at least one male member 132, 132' includes a notch 188, 188' for receiving biased latches 138, 138', as further described below. At the distal ends of the jaws 134, 134' there are provided lips 186, 186' (FIGS. 1, 3, 4, 19 and 20) configured to engage an implant to be extracted.

As shown in FIG. 2, the distal ends of jaws 134, 134' are offset from their proximal ends a distance "O" from a longitudinal axis "A" of the surgical extractor or a plane defined by the longitudinal axes of the first and second arms 102, 104. The purpose for the offset distal ends of jaws 134, 134' is that it allows them, e.g., in the context of glenosphere implant extraction, to reach around the humerus and other soft tissue or bone to access the glenoid area of the shoulder. Having the "double-angled offset" or "proximal-distal offset" of the jaws, i.e., distal ends offset from yet parallel to proximal ends, allows the device to stay parallel to a direction of extraction of the glenoid implant or glenosphere implant. Without the offset it can be difficult to firmly clamp onto the glenosphere implant and keep an extraction force in-line with the desired direction of extraction because of interference with the surrounding tissue. The shoulder is relatively a very tight area to fit instrumentation and the forces required for extraction can require stronger instruments thus increasing the size of the instrumentation. Some shoulders may be stiffer than others due to, but not limited to, prior surgeries or scar tissue or sutures or natural range of specific person's anatomy or etc., which limits the exposure in the surgery. In such cases it would be advantageous to have an offset such as that provided by the offset jaws 134, 134'.

In the alternative, the implant engaging jaws may have a "superior-inferior offset" or they can be substantially straight, i.e., the distal ends of the jaws would not have an offset from the longitudinal axis "A" of the surgical extractor. Straight jaws would be acceptable for use with shoulders that are in the process of a first-time revision surgery or are just more flexible which allow for greater exposure.

Figure 6:
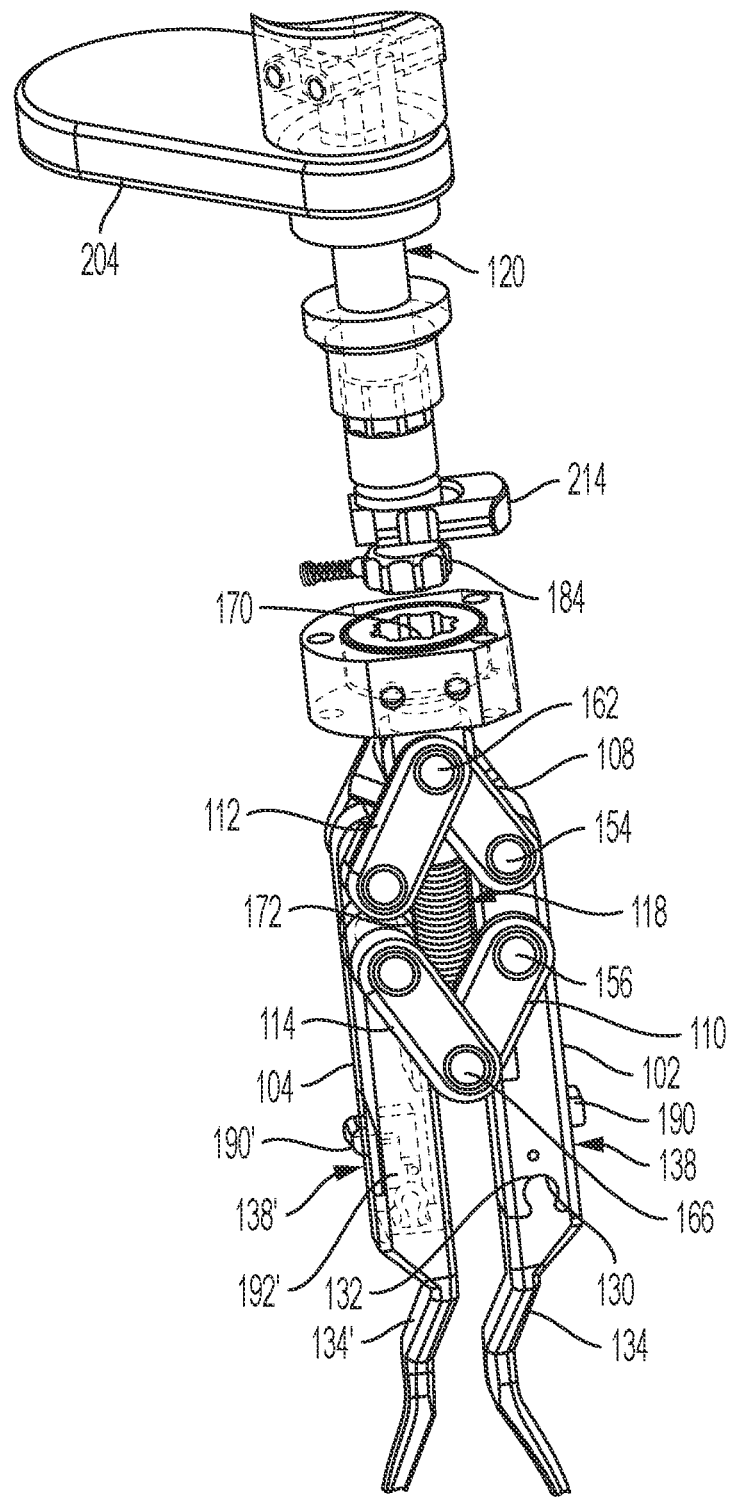
FIG. 6 is a is a partial front perspective view of the surgical extractor of FIG. 1 with certain elements omitted for clarity of illustration.
Figure 6A:
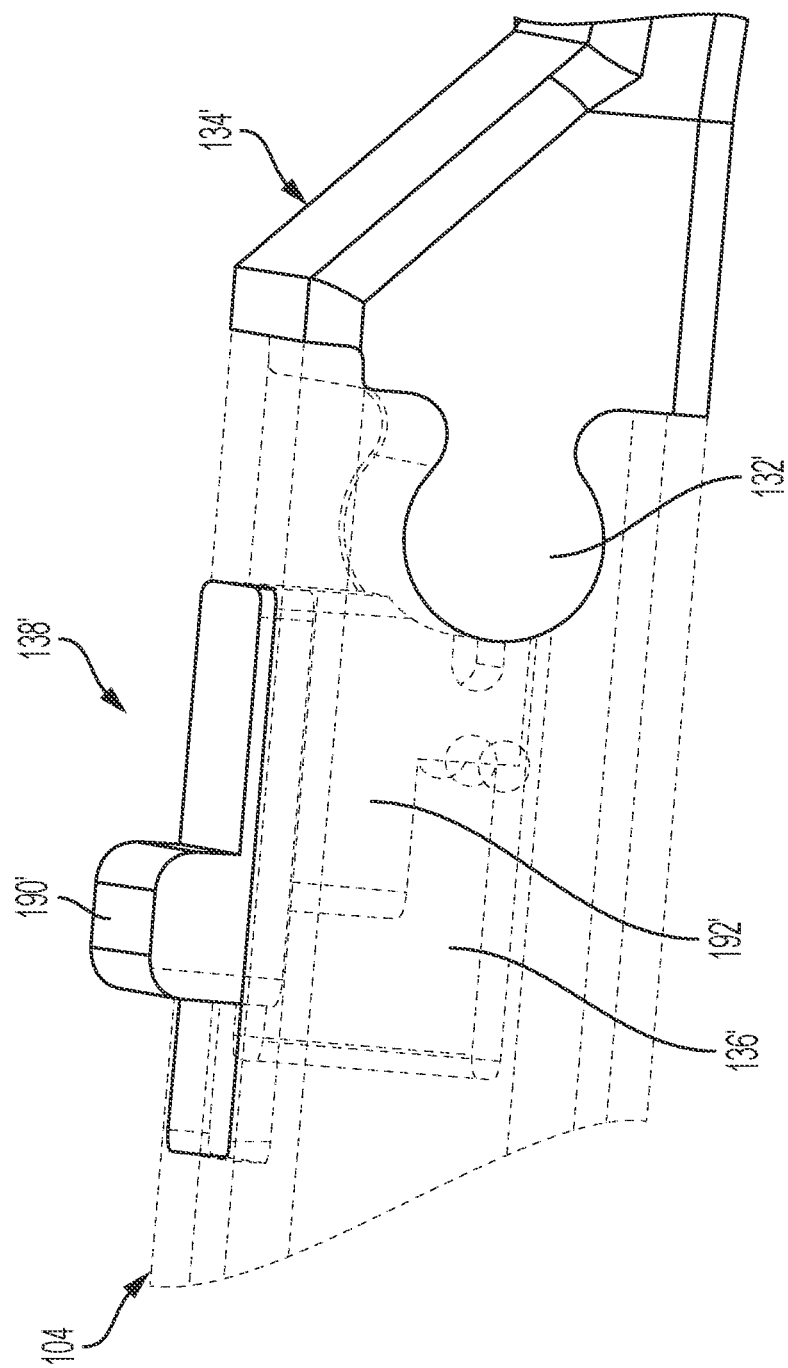
FIG. 6A is an enlarged perspective view of a biased latch carried by an arm of the surgical extractor of FIG. 1.

Referring to FIGS. 6 and 6A, the surgical extractor 100 further comprises the biased latches 138, 138'. In the illustrated example, one biased latch is carried by the first arm 102 and another biased latch is carried by the second arm 104. The biased latches releasably engage the at least one male member 132, 132' of the first and second jaws 134, 134' for connecting the first and second jaws to the first and second arms 102, 104. As shown in partial phantom line in the second arm 104 of FIGS. 6 and 6A, the biased latch 138' comprises a button 190' fixedly connected to engagement structure 192' slidably received in the slot 136' (FIGS. 6A and 12) for moving the biased latch from engagement with the proximal end of the jaw. It is understood that a similar biased latch 138 resides in slot 136 (FIG. 10) of the first arm 102. Unillustrated biasing members in the slots 136, 136' bias each of the biased latches into latching engagement with notches 188, 188' provided in male connectors 132, 132' located at proximal ends of the first and second jaws 134, 134'. The first jaw is press-fit into the first arm until the biased latch engages the jaw to secure the jaw to the first arm. The second jaw is similarly connected to the second arm.

Figure 21:
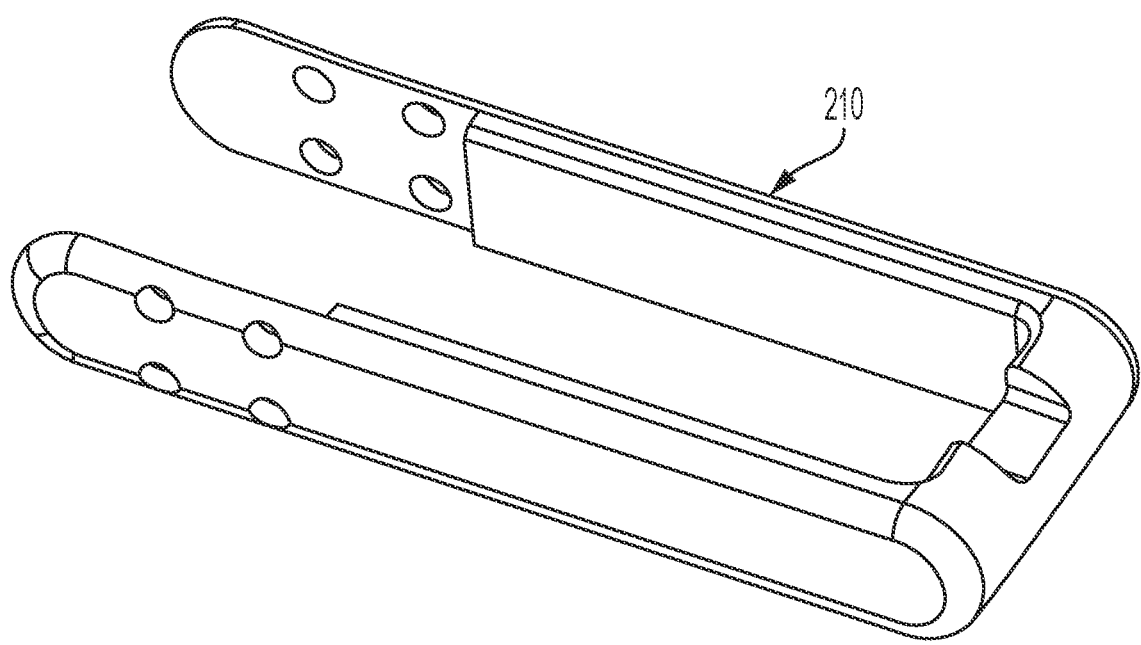
FIG. 21 is a perspective view of a bracket of the surgical extractor of FIG. 1.

Referring to FIGS. 1, 2 and 21, a generally U-shaped bracket 210 surrounds the first, second, third, fourth, fifth, sixth, seventh and eighth links 108, 110, 112, 114, 108', 110', 112' and 114'. The bracket 210 is secured to the second housing 191 by suitable fasteners 212.

Referring to FIGS. 1-4, 6, 7 and 8, the surgical extractor 100 further comprises a second actuator 214 that moves transversely to a longitudinal axis of the drive shaft 120 in the second housing 191 to engage and disengage an annular groove 182 (FIG. 17) on the drive shaft. The second actuator 214 is biased into engagement with the annular groove 182 by one or more unillustrated biasing members such as springs or the like. When the second actuator 214 is in engagement with the annular groove 182, longitudinal movement of the drive shaft 120 is prevented, as described in greater detail below.

In addition, the surgical extractor 100 further comprises a mechanism for maintaining a desired angular orientation of the T-handle 180 when extracting a glenosphere or other implant from a patient's body. As shown in FIGS. 7 and 8, the mechanism includes a biasing member 216 such as a spring or the like which, at a first end thereof, engages a detent 218 such as a ball or the like. The detent 218 is sized and shaped to be received between adjacent splines at the splined head 184 of the drive shaft 120. The second end of the biasing member engages a compression adjustment member 220 such as a set screw or the like, whereby the biasing force exerted by the biasing member 216 on the detent 218 is adjustable. Constructed as such, a user can adjust the force of the detent against the distal end of drive shaft and thus the degree of force required to rotate the T-handle 194 into a desired angular position. The biased detent 218 does not prevent the T-handle from rotating. Rather, the biased detent exerts a small biasing force between adjacent splines of the splined head 184 sufficient to prevent free rotation of the T-handle unless a rotational force is applied to the T-handle sufficient to overcome the biasing force exerted by the biasing member 216. In that event, the user can select the angular position of the T-handle and the T-handle will remain in that position until a rotational force is applied to the T-handle sufficient to overcome the biasing force exerted by the biasing member 216, whereby the T-handle may be rotated to another desired angular position.

Assembly of the surgical extractor 100 may be achieved as follows. Referring to FIG. 6, the user (e.g., a surgeon) attaches the appropriate jaws to the distal ends of the first and second arms 102, 104. Beginning with first arm 102, the male connector 132 of the jaw 134 is slid into the female socket 130 which, in turn, urges the latch 138 rearwardly against the bias of the unillustrated biasing member situated in the slot 136 (FIG. 10). Once the male connector 132 is in the female socket 130, the biasing member moves engagement structure 192 (FIG. 5) of the latch 138 forwardly until its distal end engages the notch 188 (FIG. 19) provided in the male connector 132 of the jaw 134 to lock the jaw to the distal end of the first arm 102. The user repeats the foregoing process to attach the jaw 134' to the distal end of the second arm 104. In order to remove a jaw from the first or second arm, the button 190 or 190' must be moved against the bias of the unillustrated biasing member whereby the engagement structure 192 or 192' retracts from the notch 188 or 188' and the male member can be slid out of the female opening.

Figure 18:
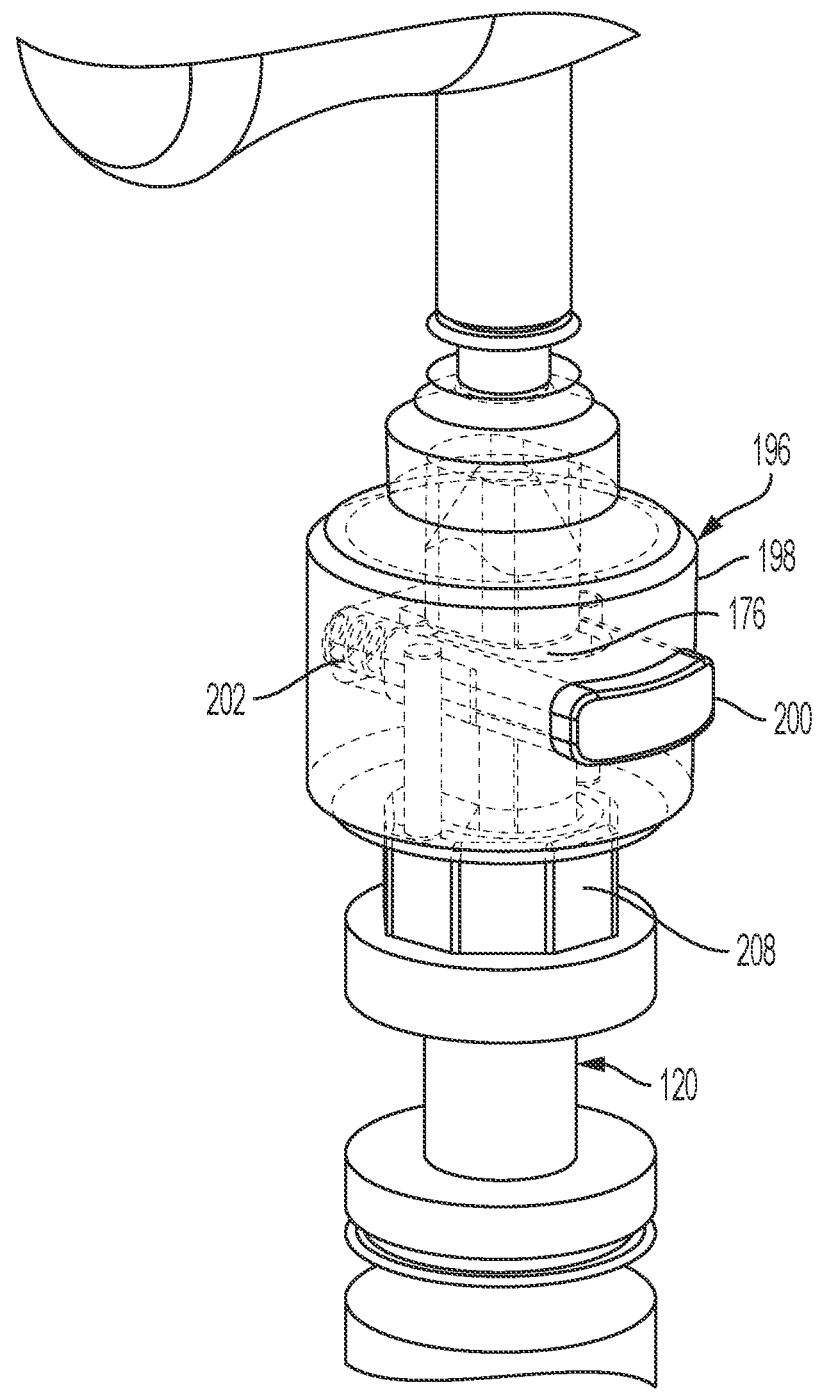
FIG. 18 is a perspective view of a push-to-connect assembly of a handle assembly of the surgical extractor of FIG. 1 with certain elements omitted for clarity of illustration.

Referring next to FIG. 18, if the first housing 198 and the T-handle 194 are disconnected from the drive shaft 120, the user depresses the first actuator 200 against the bias of biasing member 202 and slides the first housing past the proximal end 174 of the drive shaft until the actuator comes into alignment with the annular groove 176 of the drive shaft. The user then releases the first actuator 200 whereupon the biasing member 202 urges the first actuator into engagement with the annular groove. In order to release the T-handle 194 from the drive shaft, the user depresses the first actuator 200 against the bias of the biasing member 202 until the first actuator disengages the annular groove 176, whereby the first housing 198 and the T-handle 194 may be slid from the proximal end 174 of the drive shaft 120.

With the first housing 198 removed from the proximal end of the drive shaft, the strike plate 204 may be attached to the drive shaft 120. This is achieved by sliding the strike plate over the proximal end 174 of the drive shaft until the central opening 206 of the strike plate receives the polygonal portion 208 (FIG. 18) of the drive shaft to impart proper angular orientation of the strike plate on the surgical extractor. Once the strike plate is in a desired angular position, the first housing 198 and the T-handle 194 are connected to the drive shaft as described above.

The subject disclosure also provides a method for extracting an implant using the above-described surgical extractor 100. After assembling the instrument as described above, the method comprises first releasing the second actuator 214 from engagement with the annular groove 182 of the drive shaft 120. This is achieved by depressing the second actuator 214 until it is disengaged from the annular groove 182. With the second actuator in such position, the drive shaft is free to move longitudinally. As such, the user can push the T-handle 194 forwardly until the splines of the cooperating head 184 of the drive shaft 120 come into mating engagement with the socket 170 of the driven shaft 118. Once the drive shaft 120 is engaged with the driven shaft 118, the user may rotate the T-handle 194 to turn both the drive shaft and driven shaft.

The moveable screw jack nut 142 threadedly receives the threaded remainder portion 172 of the driven shaft 118. Turning of the drive shaft and the driven shaft in a first direction, e.g., clockwise, causes the distal end of the threaded remainder portion 172 of the driven shaft 118 to move the movable screw jack nut 142 toward the stationary screw jack nut 164, i.e., in the direction of arrow 1 of FIG. 13. As this occurs, the second ends of the first and third links 108, 112 pivot about the stub shaft 162 of the stationary screw jack nut 164 whereby the first ends of the first and third links diverge outwardly away from one another. Simultaneously, the second ends of the second and fourth links 110, 114 pivot about the stub shaft 166 of the movable screw jack nut 142 whereby the first ends of the second and fourth links diverge outwardly away from one another. As this occurs, the first and second arms 102, 104 move apart in parallel relationship carrying with them the jaws 134.

Once the lips 186, 186' of the jaws 134, 134' are sufficiently separated to accommodate the outer periphery of the implant to be extracted, the lips are placed beneath the implant and the user begins turning the T-handle 194 in a second, opposite direction, e.g., counterclockwise. As the user turns the T-handle in the opposite direction the movable screw jack nut 142 moves away from the stationary screw jack nut 164, i.e., in the direction of arrow 2 of FIG. 13. As this occurs, the second ends of the first and third links 108, 112 pivot about the stub shaft 162 of the stationary screw jack nut 164 whereby the first ends of the first and third links converge inwardly toward one another. Simultaneously, the second ends of the second and fourth links 110, 114 pivot about the stub shaft 166 of the movable screw jack nut 142 whereby the first ends of the second and fourth links converge inwardly toward one another. As this occurs, the first and second arms 102, 104 move toward one another in parallel relationship carrying with them the jaws 134, 134' until the lips 186, 186' of the jaws pass under the implant and the jaws come into contact with the periphery of the implant. Once the jaws are in this position, the implant may be extracted.

In order to begin the extraction process, the user pulls rearwardly on the T-handle 194 to separate the splined head 184 of the drive shaft 120 from the splined socket 170 of the driven shaft 118. The user then rotates the T-handle 194 until it reaches a comfortable position and pulls the T-handle until the detent 218 comes to rest between adjacent splines of the splined head 184 of the drive shaft. If further angular adjustment of the T-handle is necessary, the user may rotate the T-handle either clockwise or counterclockwise a desired degree until the detent comes to rest between adjacent splines of the splined head of the drive shaft to retain the T-handle in the desired angular position, e.g., a desired angular position relative to the user or patient.

Once the T-handle 194 is in the desired angular position, the user may then pull on the T-handle to exert extraction force to remove the implant from the bone in which it is embedded. In the event the user is unable to extract the implant by simply pulling on the T-handle with one hand, the user may use a hammer or mallet with the other hand to strike the underside of the strike plate 204 to generate extraction force sufficient to remove the implant from the bone in which it is embedded.

It will be appreciated by those skilled in the art that changes could be made to the exemplary embodiments described above without departing from the broad inventive concept thereof. It is to be understood, therefore, that this disclosure is not limited to the particular embodiments disclosed, but it is intended to cover modifications within the spirit and scope of the subject disclosure as disclosed above and defined by the claims.

We claim:

1. A surgical extractor comprising:
a first arm having a proximal end and a distal end;
a second arm having a proximal end and a distal end;
an adjustment assembly operatively connected to the first and second arms, the adjustment assembly including:
distinct first and second links pivotably connected to a first side of the first arm,
distinct third and fourth links pivotably connected to a first side of the second arm,
distinct fifth and sixth links pivotably connected to a second side of the first arm,
distinct seventh and eighth links pivotably connected to a second side of the second arm,
wherein each of the first, second, third, fourth, fifth, sixth, seventh and eighth links have a first end and a second end, and wherein each of the first end and the second end comprise openings, and
an adjustment mechanism including:
a driven shaft rotatable relative to the first and second arms and operable to move the first arm and the second arm toward one another into an operative position by respective inward pivoting of the first and second links and of the third and fourth links, and
a drive shaft for driving rotation of the driven shaft; and
a bracket extending alongside the first, second, third, fourth, fifth, sixth, seventh and eighth links.

2. The surgical extractor of claim 1, further comprising:
a handle assembly operably attachable to the adjustment mechanism for rotating the drive shaft;
a first jaw attachable to the distal end of the first arm; and
a second jaw attachable to the distal end of the second arm.

3. The surgical extractor of claim 2, wherein the handle assembly comprises a push-to-connect assembly structured to releasably couple to a proximal end of the drive shaft.

4. The surgical extractor of claim 3, wherein the drive shaft includes an annular groove adjacent the proximal end thereof.

5. The surgical extractor of claim 4, wherein the push-to-connect assembly comprises an actuator operable to move transversely to a longitudinal axis of the drive shaft to engage and disengage the annular groove.

6. The surgical extractor of claim 5, wherein the push-to-connect assembly further comprises a biasing member biasing the actuator into engagement with the annular groove.

7. The surgical extractor of claim 2, wherein the handle assembly comprises a T-handle.

8. The surgical extractor of claim 1, wherein the driven shaft includes a proximal end and a threaded remainder portion, and wherein the proximal end is spaced from the proximal ends of the first and second arms.

9. The surgical extractor of claim 8, further comprising a stationary screw jack nut that rotatably receives the driven shaft, and a moveable screw jack nut that threadedly receives the threaded remainder portion.

10. The surgical extractor of claim 9, wherein second ends of the first and third links are pivotably connected to the stationary screw jack nut, and wherein second ends of the second and fourth links are pivotably connected to the moveable screw jack nut.

11. The surgical extractor of claim 1, wherein a proximal end of the driven shaft includes a socket.

12. The surgical extractor of claim 11, wherein a distal end of the drive shaft includes a cooperating head to engage with the socket of the driven shaft.

13. The surgical extractor of claim 1, further comprising a strike plate including:

a substantially planar member having a first striking surface and a second striking surface opposite the first striking surface; and
a multisided through opening configured to receive a multisided shaft portion of the surgical extractor.

14. The surgical extractor of claim 1, further comprising:
a jaw having a proximal end configured for attachment to the distal end of the first arm and a distal end configured for engaging an implant; and
a biased latch adjacent the distal end of the first arm for releasably engaging the proximal end of the jaw.

15. The surgical extractor of claim 14, further comprising at least one male member carried by the proximal end of the jaw and at least one female opening at the distal end of the first arm for receiving the at least one male member.

16. The surgical extractor of claim 15, wherein the biased latch releasably engages the at least one male member.

17. The surgical extractor of claim 16, wherein the at least one male member includes a notch for receiving the biased latch.

18. The surgical extractor of claim 14, wherein the biased latch includes a button for moving the biased latch from engagement with the proximal end of the jaw.

* * * * *